US008715721B2

(12) United States Patent
Oshlack et al.

(10) Patent No.: US 8,715,721 B2
(45) Date of Patent: *May 6, 2014

(54) CONTROLLED RELEASE HYDROCODONE

(71) Applicant: Purdue Pharma L.P., Stamford, CT (US)

(72) Inventors: Benjamin Oshlack, New York, NY (US); Hua-Pin Huang, Englewood Cliffs, NJ (US); John K. Masselink, Old Tappan, NJ (US); Alfred Tonelli, Congers, NY (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,069

(22) Filed: May 23, 2013

(65) Prior Publication Data

US 2013/0295177 A1 Nov. 7, 2013

Related U.S. Application Data

(60) Continuation of application No. 13/721,293, filed on Dec. 20, 2012, which is a continuation of application No. 13/535,996, filed on Jun. 28, 2012, now Pat. No. 8,361,499, which is a continuation of application No. 12/914,054, filed on Oct. 28, 2010, now Pat. No. 8,231,898, which is a division of application No. 12/378,586, filed on Feb. 17, 2009, now Pat. No. 8,142,811, which is a continuation of application No. 10/660,349, filed on Sep. 11, 2003, now Pat. No. 7,514,100, which is a continuation of application No. 10/016,651, filed on Oct. 30, 2001, now Pat. No. 6,733,783.

(60) Provisional application No. 60/244,424, filed on Oct. 30, 2000.

(51) Int. Cl.
- *A61K 9/48* (2006.01)
- *A61K 9/20* (2006.01)
- *A61K 9/14* (2006.01)
- *A61K 9/24* (2006.01)
- *A61K 31/44* (2006.01)
- *A01N 43/00* (2006.01)

(52) U.S. Cl.
USPC .......... 424/451; 424/464; 424/472; 424/484; 514/282; 514/161

(58) Field of Classification Search
USPC .......... 424/451, 464, 484, 472; 514/282, 161
See application file for complete search history.

(56) References Cited

U.S. PATENT DOCUMENTS

| | | | |
|---|---|---|---|
| 2,738,303 A | 3/1956 | Blythe | 167/82 |
| 3,634,584 A | 1/1972 | Poole | 424/21 |
| 3,845,770 A | 11/1974 | Theeuwes et al. | 128/260 |
| 3,870,790 A | 3/1975 | Lowey et al. | 424/19 |
| 3,916,889 A | 11/1975 | Russell | 128/145.8 |
| 3,916,899 A | 11/1975 | Theeuwes et al. | 128/260 |
| 4,063,064 A | 12/1977 | Saunders et al. | 219/121 L |
| 4,088,864 A | 5/1978 | Theeuwes et al. | 219/121 LM |
| 4,132,753 A | 1/1979 | Blichare et al. | 264/25 |
| 4,377,568 A | 3/1983 | Chopra | 424/31 |
| 4,385,078 A | 5/1983 | Onda et al. | 427/3 |
| 4,389,393 A | 6/1983 | Schor et al. | 424/19 |
| 4,421,736 A | 12/1983 | Walters | 424/19 |
| 4,443,428 A | 4/1984 | Oshlack et al. | 424/22 |
| 4,464,378 A | 8/1984 | Hussain | 424/260 |
| 4,483,847 A | 11/1984 | Augart | 424/22 |
| 4,520,172 A | 5/1985 | Lehmann et al. | 525/369 |
| 4,548,990 A | 10/1985 | Mueller et al. | 525/123 |
| 4,557,925 A | 12/1985 | Lindahl et al. | 424/19 |
| 4,600,645 A | 7/1986 | Ghebre-Sellassie et al. | 428/403 |
| 4,609,542 A | 9/1986 | Panoz et al. | 424/19 |
| 4,708,874 A | 11/1987 | De Haan et al. | 424/470 |
| 4,728,513 A | 3/1988 | Ventouras | 424/461 |
| 4,797,410 A | 1/1989 | El-Fakahany | 514/356 |
| 4,806,337 A | 2/1989 | Snipes et al. | 71/65 |
| 4,828,836 A | 5/1989 | Elger et al. | 424/419 |
| 4,834,984 A | 5/1989 | Goldie et al. | 424/488 |
| 4,834,985 A | 5/1989 | Elger et al. | 424/488 |
| 4,844,907 A | 7/1989 | Elger et al. | 424/465 |
| 4,844,909 A | 7/1989 | Goldie | 424/490 |
| 4,861,596 A | 8/1989 | Curtiss et al. | |
| 4,861,598 A | 8/1989 | Oshlack et al. | 424/468 |
| 4,894,234 A | 1/1990 | Sharma et al. | 424/480 |
| 4,935,246 A | 6/1990 | Ahrens | 424/490 |
| 4,959,219 A | 9/1990 | Chow et al. | |
| 4,970,075 A | 11/1990 | Oshlack et al. | 424/451 |
| 4,983,730 A | 1/1991 | Domeshek et al. | 536/69 |
| 4,990,341 A | 2/1991 | Goldie et al. | 424/484 |

(Continued)

FOREIGN PATENT DOCUMENTS

| | | |
|---|---|---|
| AU | 9047732 | 7/1990 |
| AU | 9341654 | 2/1995 |

(Continued)

OTHER PUBLICATIONS

Claims pending in U.S. Appl. No. 13/721,293 on May 29, 2013.

(Continued)

*Primary Examiner* — Aradhana Sasan
(74) *Attorney, Agent, or Firm* — Davidson, Davidson & Kappel, LLC

(57) ABSTRACT

A solid oral controlled-release dosage form of hydrocodone is disclosed, the dosage form comprising an analgesically effective amount of hydrocodone or a pharmaceutically acceptable salt thereof, and controlled release material.

34 Claims, No Drawings

(56) References Cited

U.S. PATENT DOCUMENTS

| | | | |
|---|---|---|---|
| 4,996,047 A | 2/1991 | Kelleher et al. | |
| 5,007,790 A | 4/1991 | Shell | 424/451 |
| 5,019,397 A | 5/1991 | Wong et al. | 424/473 |
| 5,023,089 A | 6/1991 | Sakamoto et al. | 424/502 |
| 5,024,842 A | 6/1991 | Edgren et al. | 424/473 |
| 5,026,560 A | 6/1991 | Makino et al. | 424/494 |
| 5,030,400 A | 7/1991 | Danielsen et al. | 264/101 |
| 5,068,110 A | 11/1991 | Fawzi et al. | 424/461 |
| 5,071,646 A | 12/1991 | Malkowska et al. | 424/497 |
| 5,122,384 A | 6/1992 | Paradissis et al. | 424/451 |
| 5,126,145 A | 6/1992 | Evenstad et al. | 424/465 |
| 5,132,142 A | 7/1992 | Jones et al. | 427/196 |
| 5,133,974 A | 7/1992 | Paradissis et al. | 424/480 |
| 5,167,964 A | 12/1992 | Muhammad et al. | 424/482 |
| 5,169,645 A | 12/1992 | Shukla et al. | 424/499 |
| 5,178,868 A | 1/1993 | Malmqvist-Granlund et al. | 424/490 |
| 5,196,203 A | 3/1993 | Boehm | 424/469 |
| 5,202,128 A | 4/1993 | Morella et al. | 424/469 |
| 5,206,030 A | 4/1993 | Wheatley et al. | 424/490 |
| 5,219,575 A | 6/1993 | Van Bommel et al. | 424/490 |
| 5,248,516 A | 9/1993 | Wheatley et al. | 427/3 |
| 5,258,436 A | 11/1993 | Wheatley et al. | 524/388 |
| 5,266,331 A | 11/1993 | Oshlack et al. | 424/468 |
| 5,273,760 A | 12/1993 | Oshlack et al. | 424/480 |
| 5,283,065 A | 2/1994 | Doyon et al. | 424/467 |
| 5,286,493 A | 2/1994 | Oshlack et al. | 424/468 |
| 5,292,461 A | 3/1994 | Juch et al. | 264/37 |
| 5,321,012 A | 6/1994 | Mayer et al. | 514/25 |
| 5,330,766 A | 7/1994 | Morella et al. | 424/490 |
| 5,356,467 A | 10/1994 | Oshlack et al. | |
| 5,378,474 A | 1/1995 | Morella et al. | 424/469 |
| 5,384,130 A | 1/1995 | Kamada | 424/461 |
| 5,411,745 A | 5/1995 | Oshlack et al. | 424/456 |
| 5,456,923 A | 10/1995 | Nakamichi et al. | 424/489 |
| 5,460,826 A | 10/1995 | Merrill et al. | 424/470 |
| 5,472,712 A | 12/1995 | Oshlack et al. | 424/480 |
| 5,478,577 A | 12/1995 | Sackler et al. | 424/489 |
| 5,500,227 A | 3/1996 | Oshlack et al. | 424/476 |
| 5,502,058 A | 3/1996 | Mayer et al. | 514/289 |
| 5,508,040 A | 4/1996 | Chen | |
| 5,508,042 A | 4/1996 | Oshlack et al. | 424/468 |
| 5,518,730 A | 5/1996 | Fuisz | |
| 5,520,931 A | 5/1996 | Persson et al. | 424/473 |
| 5,549,912 A | 8/1996 | Oshlack et al. | 424/468 |
| 5,580,578 A | 12/1996 | Oshlack et al. | 424/468 |
| 5,593,695 A | 1/1997 | Merrill et al. | 424/480 |
| 5,601,842 A | 2/1997 | Bartholomaeus | 424/464 |
| 5,614,218 A | 3/1997 | Olsson et al. | 424/456 |
| 5,629,011 A | 5/1997 | Illum | 424/434 |
| 5,637,320 A | 6/1997 | Bourke et al. | 424/489 |
| 5,639,476 A | 6/1997 | Oshlack et al. | |
| 5,656,295 A | 8/1997 | Oshlack et al. | 424/468 |
| 5,667,805 A | 9/1997 | Merrill et al. | 424/473 |
| 5,670,172 A | 9/1997 | Buxton et al. | 424/495 |
| 5,672,360 A | 9/1997 | Sackler et al. | 424/490 |
| 5,681,585 A | 10/1997 | Oshlack et al. | 424/494 |
| 5,837,284 A | 11/1998 | Mehta et al. | |
| 5,843,480 A | 12/1998 | Miller et al. | 424/484 |
| 5,849,240 A | 12/1998 | Miller et al. | 264/460 |
| 5,866,161 A | 2/1999 | Childers et al. | |
| 5,879,705 A | 3/1999 | Heafield et al. | 424/464 |
| 5,891,471 A | 4/1999 | Miller et al. | 424/468 |
| 5,958,452 A | 9/1999 | Oshlack et al. | |
| 5,958,459 A | 9/1999 | Chasin et al. | 424/490 |
| 5,965,161 A | 10/1999 | Oshlack et al. | |
| 5,965,163 A | 10/1999 | Miller et al. | 424/468 |
| 5,968,551 A | 10/1999 | Oshlack et al. | 424/456 |
| 6,103,261 A | 8/2000 | Chasin et al. | 424/459 |
| 6,143,322 A | 11/2000 | Sackler et al. | 424/459 |
| 6,228,398 B1 | 5/2001 | Devane et al. | |
| 6,264,983 B1 | 7/2001 | Upadhyay | 424/464 |
| 6,294,195 B1 | 9/2001 | Oshlack et al. | |
| 6,491,945 B1 | 12/2002 | Childers et al. | |
| 6,572,885 B2 | 6/2003 | Oshlack et al. | |
| 6,607,750 B2 | 8/2003 | Upadhyay et al. | 424/464 |
| 6,699,502 B1 | 3/2004 | Fanara et al. | 424/484 |
| 6,730,325 B2 | 5/2004 | Devane et al. | |
| 6,733,783 B2 | 5/2004 | Oshlack et al. | 424/473 |
| 6,793,936 B2 | 9/2004 | Devane et al. | |
| 6,902,742 B2 | 6/2005 | Devane et al. | |
| 7,943,174 B2 | 5/2011 | Oshlack et al. | 424/464 |
| 2004/0266807 A1 | 12/2004 | Oshlack et al. | |
| 2006/0240105 A1 | 10/2006 | Devane et al. | |
| 2008/0102121 A1 | 5/2008 | Devane et al. | |
| 2008/0226734 A1 | 9/2008 | Jenkins et al. | |
| 2009/0149479 A1 | 6/2009 | Jenkins et al. | |
| 2011/0262532 A1 | 10/2011 | Oshlack et al. | 424/401 |
| 2012/0164220 A1 | 6/2012 | Huang | |
| 2012/0165358 A1 | 6/2012 | Cruz et al. | |

FOREIGN PATENT DOCUMENTS

| | | |
|---|---|---|
| AU | 199944493 | 10/1999 |
| CA | 2082573 | 11/1992 |
| CA | 2131350 A1 | 1/1994 |
| EP | 0097523 A2 | 1/1984 |
| EP | 0097523 B1 | 1/1984 |
| EP | 0108218 | 5/1984 |
| EP | 0147780 A2 | 7/1985 |
| EP | 0235986 A1 | 9/1987 |
| EP | 0235986 B1 | 9/1987 |
| EP | 0235986 B2 | 9/1987 |
| EP | 0253104 A1 | 1/1988 |
| EP | 0253104 B1 | 1/1988 |
| EP | 0267702 A3 | 5/1988 |
| EP | 0271193 B1 | 6/1988 |
| EP | 0327295 A2 | 8/1989 |
| EP | 0361680 B1 | 4/1990 |
| EP | 0361910 A1 | 4/1990 |
| EP | 0377517 A2 | 7/1990 |
| EP | 0377518 A2 | 7/1990 |
| EP | 0377518 A3 | 7/1990 |
| EP | 0388954 A2 | 9/1990 |
| EP | 0388954 A3 | 9/1990 |
| EP | 0388954 B1 | 9/1990 |
| EP | 0377518 A3 | 10/1990 |
| EP | 0415693 A1 | 3/1991 |
| EP | 0430287 B1 | 6/1991 |
| EP | 0452145 A2 | 10/1991 |
| EP | 0532348 A2 | 3/1993 |
| EP | 0532348 A3 | 3/1993 |
| EP | 0532348 B1 | 3/1993 |
| EP | 0533297 A1 | 3/1993 |
| EP | 0534628 A1 | 3/1993 |
| EP | 0534628 B1 | 3/1993 |
| EP | 0535841 A1 | 4/1993 |
| EP | 0546676 A1 | 6/1993 |
| EP | 0548448 A1 | 6/1993 |
| EP | 0553392 A1 | 8/1993 |
| EP | 0580860 A1 | 2/1994 |
| EP | 0609961 A1 | 8/1994 |
| EP | 0636370 A1 | 2/1995 |
| EP | 0636370 B1 | 2/1995 |
| EP | 0647448 | 4/1995 |
| EP | 0665010 A1 | 8/1995 |
| EP | 1442745 | 8/2004 |
| GB | 2053681 B | 2/1981 |
| GB | 2170104 A | 7/1986 |
| GB | 2178313 A | 2/1987 |
| JP | 04081086 | 4/1992 |
| WO | WO9201446 A1 | 2/1992 |
| WO | WO9202209 A1 | 2/1992 |
| WO | WO9206679 A1 | 4/1992 |
| WO | WO9208459 A1 | 5/1992 |
| WO | WO9304675 A1 | 3/1993 |
| WO | WO9307859 A1 | 4/1993 |
| WO | WO9307861 A1 | 4/1993 |
| WO | 93/10765 | 6/1993 |
| WO | WO9310765 | 6/1993 |
| WO | WO9318753 A1 | 9/1993 |
| WO | WO9403160 | 2/1994 |
| WO | WO9403161 | 2/1994 |
| WO | WO9405262 A1 | 3/1994 |

(56) References Cited

FOREIGN PATENT DOCUMENTS

| | | |
|---|---|---|
| WO | WO9422431 A1 | 10/1994 |
| WO | 9514460 | 6/1995 |
| WO | WO9600066 A1 | 1/1996 |
| WO | WO9601629 A1 | 1/1996 |
| WO | 9608253 | 3/1996 |
| WO | 9614058 | 5/1996 |
| WO | WO9614058 A1 | 5/1996 |
| WO | 9733566 | 9/1997 |
| WO | 9733566 A2 | 9/1997 |
| WO | 9841194 | 9/1998 |
| WO | 9932120 | 7/1999 |
| WO | 0132148 | 5/2001 |
| WO | 02087512 | 11/2002 |

OTHER PUBLICATIONS

Claims pending in U.S. Appl. No. 13/901,761 on May 29, 2013.
Santus G., and Baker. R.W., "Osmotic drug delivery: a review of the patent literature," J Controlled Release (1995) vol. 35 pp. 1-21.
Hansch C et al.,"Comprehensive Medicinal Chemistry, vol. 5 Biopharmaceutics," Rational Design, Mechanistic Study and Therapeutic Application of Chemical Compounds, Oxford, Pergamon Press, GB, vol. 5, 1990, pp. 251-278, XP008054499.
Ratain M J et al., "Population Pharmacodynamic Study of Amonafide: A Cancer and Leukemia Group B Study," Journal of Clinical Oncology, Grune and Stratton, New York, NY, US, vol. 13, No. 3, Mar. 1995, pp. 741-747, XP008044974 ISSN: 0732-183X.
Database Medline [Online] US National Library of Medicine (NLM), Bethesda, MD, US; Aug. 1994, Yasuhara H: "Ethnic factors in evaluation of drug efficacy and safety," XP002350633 Database accession No. NLM7927070.
Setiabidu R et al., "Dapsone N-Acetylation, Metoprolol, Alpha-Hydroxylation, and S-Mephenytoin 4-Hydroxylation Polymorphisms in an Indonesian Population: A Cocktail and Extended Phenotyping Assessment Trail," Clinical Pharmacology & Therapeutics, Mosby-Year Book, St Louis, MO, US, vol. 56, No. 2, Aug. 1994, pp. 142-153, XP008044975 ISSN: 0009-9236.
"Helsinki Declaration" Online Ethics Center, [Online] Apr. 5, 2005, XP002350634 Retrieved from the Internet: URL:http://onlineethics.org/reseth/helsink i.html> retrieved on Oct. 25, 2005.
Castensen et al., "USP Dissolution IV:Comparison of Methods," J. Pham. Sci 1978, 67(9), pp. 1303-1307.
Encarta World English Dictionary [North American Edition] 2006 Microsoft Incorporation "Matrix", p. 1, definition 2, http://encarta.msn.com/encnet/features/dictionary/DictionaryResults.aspx?-refid=1861678516 retrieved on Apr. 30, 2006.
Wiktionary, "dispersed," p. 1, http://en.wiktionary.org/wiki/disperse retrived on Apr. 30, 2006.
Abraham Sunshine et al., "Analgesic Oral Efficacy of Tramadol Hydrochloride in Postoperative Pain," Clin. Pharmacol. Ther., vol. 51, Jun. 1992, pp. 740-746.
E.Beubler, "Medikamentose Schmerztherapie: Kriterien, Moglichkeiten, Risken," Therapiewoche Osterreich, 7,2 (1992), pp. 1-15, English translation.
Gourlay, et al., "Influence of a High-Fat Metal on The Absorption of Morphine From Oral Solutions," Clin. Pharmacol. Ther., vol. 46, Oct. 1989, pp. 463-468.
Geoffrey K. Gourlay, et al.,"The Reproducibility of Bioavailability of Oral Morphine from Solution Under Fed and Fasted Conditions," Journal of Pain and Symtoms Management, vol. 6., No. 7, Oct. 1991, pp. 431-436.
Robert F. Kaiko, et al., "Controlled-Release Morphine Bioavailability (MS Contin Tablets) in the Presence and Absence of Food," The Hospice Journal, vol. 6(4) 1990, pp. 17-30.
Yokokawa N., et al., "Relationship between plasma concentration of morphine and analgesic effectiveness," Postgrad Med J. (1991) 67 (Suppl. 2) pp. S50-S54.
Physicians Desk Reference 1994, 48th Edition, pp. 1821-1824.
D.L. Munday, et al., "Changes in Drug Release Rate 2. Effect of Temperature and Relative Humidity on Polymeric Film Coatings," 5th Cong. Int. Tech. Pharm., 1989, vol. 2, pp. 55-60.
A Protocol for a clinical study entitled "A Randomized, Double-Blind, Parallel-Group Study comparing the Efficacy and Safety of Kapanol® to MS Contin® in the Management of Patients with Moderate to Severe Cancer Pain" ("The Protocol"). The date of the Protocol is indicated as Feb. 10, 1992 and it bears COD No. 14556. The sponsor of the study is indicated to be Faulding Pharmaceuticals, an Australian company.
Certain Patients Diary Cards, Drug Disposition Records, Case Reports Forms and listing which apparently correlates patient randomization number with the treatment of dosing regimen assigned to each patient, 2003.
Patient consent forms, apparently for four study participants, 2003.
Investigator agreements between the study organizers and certain of the principal investigators, 2003.
Abstracts from the Twelfth Annual Congress of the Oncology Nursing Society, May 1987, in Clinical Nursing Forum Supplement vol. 14 (2), p. 112, 1987.
J. Lapin et al., "Cancer Pain Management with a Controlled Release Oral Morphine Preparation," Pain and Symptom Manag., vol. 4 (3), pp. 146-151,1989.
J. Lapin et al., "Guidelines for Use of Controlled Release Oral Morphine in Cancer Pain Management," Cancer Nursing, vol. 12 (4), pp. 202-208, (1989).
R.K. Kaiko, "The Pre-and Postoperative Use of Controlled-Release Morphine (MS Contin Tablets): A Review of the Published Literature," Medical Department, The Pudue Frederick Company, Royal Society of Medical Services, International Congress, Symposium Services, No. 149, pp. 147-160 (1989).
H.F. Stowey et al., "Effect of Premedication with Controlled-Release Oral Morphine on Postoperative Pain," Anesthesia, 1985, vol. 40, pp. 438-440.
MSContin—Frequency of Daily Dosing, Jan.-Nov. 1990.
R.K. Portenoy, et al., "A Randomized, Double-Blind, Double-Dummy, Crossover Study Comparing the Pharmacokinetics and Pharmacodynamics of Kapanol® Capsules Given Every 24 hours and Every 12 hours with MS Contin® Tablets Given Every 12 Hours in the Management of Patients with Moderate to Severe Chronic Pain," Memorial Hospital IRB Protocol pp. 379-381, 1993.
7th World Congress on Pain, Abstracts 997-1001, Aug. 26, 1993.
Advertisement: Raxanol SR., 1988 Roxane Labs, Inc.
T. Hunt and R. Kaiko, "Comparison of the Pharmacokinetic Profiles of Two Oral Controlled-Release Morphine Formulation in Healthy Young Adults," Clin. Thera., vol. 13, No. 4, pp. 482-488, 1991.
S. Bloomfield, et al., "Analgesic Efficacy and Potency of Two Oral Controlled-Release Morphine Preparations Clin. Pharmacol," Ther., vol. 53, No. 4, pp. 469-478, 1993.
Advertisement: MS Contin 1986, 1987 The Purdue Frederick Company.
Sustained Release Medications, Noyes Data Corp., pp. 3,4, 10-15, 96-99, 335-337 (1980).
Flanders, P., et al., "The Control of Drug Release From Conventional Melt Granulation Matrices," Drug Development and Industrial Pharmacy, vol. 13, No. 6, pp. 1001-1022 (1987).
McTaggart, Celia M., et al., "The evaluation of formulation and processing conditions of a melt granulation process," International Journal of Pharmaceutics, vol. 19, pp. 139-148 (1984).
Schaefer, T., et al., "Melt granulation in a laboratory scale high shear mixer," Drug Development and Industrial Pharmacy, vol. 16, No. 8, pp. 1249-1277 (1990).
Thomsen, L. Juul, et al., "Prolonged Release Matrix Pellets Prepared by Melt Pelletization I. Process Variables," Drug Development and Industrial Pharmacy, vol. 19, No. 15, pp. 1867-1887 (1993).
Thomsen, L. Juul, "Prolonged Release Matrix Pellets prepared by Melt Pelletization II. Hydrophobic Substances as Meltable Binders," vol. 20, No. 77, pp. 1179-1197 (1994).
Thomsen, L. Juul, "Utilizing melt pelletization technique for the preparation of prolonged release products," Pelletization, (material elaborated by assistant prof. Lars Jull Thomsen, Department of Pharmaceutics, Royal Danish School of Pharmacy of the DIE course "Pelletization Technology," Nov. 1992, 106 pages plus 3 appendices.

(56) References Cited

OTHER PUBLICATIONS

Thomsen, L. Juul, "Prolonged Release Matrix Pellets Prepared by Melt Pelletization. Part IV: Drug Particles Size, and Binder Composition," Pharmaceutical Technology Europa, pp. 19-24 (Oct. 1994).
Maccarrone C. et al.," Single Dose Pharmacokinetics of Kapanol™ a New Oral Sustained-Release Morphine Formulation,"Clinical Drug Investigation 1994:7 (5) 262-274.
West R. J., et al., "Single dose pharmacokinetics of a new oral sustained release morphine formulation, Kapanol™ capsules," (Abstract 997) International Association for the Study of Pain, 7th World Congress on Pain. Paris, Aug. 22-27, 1993 (Data on file, Glaxo Australia, F.H. Faulding).
Gourlay GK, et al., "A comparison of Kapanol™ (A new sustained release morphine formulation), MST Contius® and morphine solution in cancer patients: pharmacokinetics aspects," (Abstract 998) International Association for the Study of Pain, 7th World Congress on Pain Paris, Aug. 22-27, 1993 (Data on file, Glaxo Australia, F.H. Faulding).
Cherry DA, et al., "A comparison of Kapanol™ (a new sustained release morphine formulation), MST Continus™ and morphine solution in cancer patients: Morphine metabolite profiles and renal function," (Abstract 999) International Association for the Study of Pain, 7th World Congress on Pain, Paris Aug. 22-27, 1993 (Data on file, Glaxo Australia, F.H. Faulding).
Plummer JL, et al., "A comparison of Kapanol™ (a new sustained release morphine formulation) MST Continus™ and mophine solution in cancer patients: pharmcodynamic aspects," (Abstract 1000) International Association for the Study of Pain, 7th World Congress on Pain, Paris, Aug. 22-27, 1993 (Data on file, Glaxo Australia, F.H. Faulding).
Toner G, Cramond T, Bishop, et al., "Randomized double blind, phase III crossover study of a new sustained-release oral mophine formulation, Kapanol™ capsules," (Abstract 1001) International Association for the Study on Pain, Paris, Aug. 22-27, 1993 (Data on file, Glaxo Australia, F.H. Faulding).
Cherry DA, et al., "Once a Day (i.e. 24 Hourly) Kapanol™, A New Sustained Release Morphine Formulation, in the Treatment of Cancer Pain: Morphine Metabolite Profiles," European Journal of Cancer; Part A General Topics 1995; 31 (S5) Suppl:S184 Abs 884, European Conference on Clinical Oncology and Cancer Nursing, Paris, Oct. 29-Nov. 2, 1995.
Gourlay, et al., "Once a Day (i.e. 24 Hourly) Kapanol™, A New Sustained Release Morphine Formulation, In the Treatment of Cancer Pain: Pharmacokinetic Aspects," European Journal of Cancer; Part A General Topics 1995:31 (S5) Suppl: S187 Abs 897, European Conference on Clinical Oncology and Cancer Nursing, Paris, Oct. 29-Nov. 2, 1995.
Broomhead, et al., "Kadian™/Kapanol™—A Once Daily Mophine Formulation," European Journal of Cancer; Part A General Topics 1995:31 (S5) Suppl: S182 Abs 873, European Conference on Clinical Onclology and Cancer Nursing, Paris, Oct. 29-Nov. 2, 1995.
Gourlay et al., "Proceedings of the 7th World Congress on Pain; A comparison of Kapanol (a New Sustained-Release Morphine Formulation), MST Continus, and Morphine Solution in Cancer Patients,"
Pharmacolinetic Aspects of Morphine and Morphine Metabolites Progress in Pain Research and Management vol. 2 pp. 631-643, 1993.
MS Contin—Frequency of Daily Dosing (NDTI)—Jun. 1991-May 1992.
Kaiko R.F., "Clinical Protocol and Role of Controlled Release Morphine in the Surgical Patient," Anesthesiology and Pain Management 1991 pp. 193-212.
Kaiko et al., "A Single-Dose Study of the Effect of Food Ingestion and Timing of Dose Administration on the Pharmacokinetic Profile of 30-mg Sustained-Release Morphine Sulfate Tablets," Current Terapeutic Research, vol. 47, No. 5, May 1990, pp. 869-878.
European Search Report issued in connection with European Application No. 10177508.8-2123 on Sep. 11, 2010.
"The Merck Manual," Merck and Co., p. 4711 (1989).
Encyclopedia of Controlled Drug Delivery, vol. 1, "In vitro-in vivo correlation," pp. 425-435 (1999).
Encyclopedia of Controlled Drug Delivery, vol. 2, "Oral drug delivery, small intestine & colon," pp. 698-728 (1999).
Guidance for Industry, "Extended Release Oral Dosage Forms: Development, Evaluation, and Application of In Vitro/ In vivo Correlation" ( FDA, 1997).
Opinion Expressed by the Board of Appeal in the Summons to Oral Proceedings in Case EP02026247 ( May 24, 2011).
Goodman and Gilman's, The Pharmacological Basis of Therapeutics, pp. 7-8 (1990).
Office Action issued on May 24, 2011, in connection with European Application No. 10 179 087.1-2123
Office Action issued on Jul. 27, 2012, in connection with European Application No. 01 992 565.0-2123.
Office Action issued on Jul. 27, 2012, in connection with European Application No. 10 177 508.8-2123.
Office Action issued on Jul. 27, 2012, in connection with European Application No. 10 179 086.3-2123.
Zohydro ER Package Insert revised Oct. 2013.
Advisory Committee Briefing Document, NDA 20-2880, Zohydro™ ER Hydrocodone Bitartrate Extended-Release Capsules, Anesthetic and Analgesic Drug Products Advisory Committee, Dec. 7, 2012.
FDA Response to a Citizen Petition, Docket No. FDA-2013-P-0703, Oct. 25, 2013.
Summons to attend oral proceedings issued on Jun. 5, 2013, in connection with European Patent Application No. 10180984.6.
Summons to attend oral proceedings issued on Jun. 5, 2013, in connection with European Patent Application No. 10181032.3.
Summons to attend oral proceedings issued on Jun. 5, 2013, in connection with European Patent Application No. 10177508.8.
Summons to attend oral proceedings issued on Jun. 5, 2013, in connection with European Patent Application No. 01992565.0.
Summons to attend oral proceedings issued on Jun. 5, 2013, in connection with European Patent Application No. 10179087.1.
Summons to attend oral proceedings issued on Jun. 5, 2013, in connection with European Patent Application No. 10179086.3.
Claims pending in U.S. Appl. No. 13/833,263 on Nov. 19, 2013.
Claims pending in U.S. Appl. No. 14/094,968 on Dec. 9, 2013.
Claims pending in U.S. Appl. No. 13/833,263 on Dec. 9, 2013.

CONTROLLED RELEASE HYDROCODONE

This application is a continuation of U.S. patent application Ser. No. 13/721,293, filed on Dec. 20, 2012, which is a continuation of U.S. patent application Ser. No. 13/535,996, filed on Jun. 28, 2012, now U.S. Pat. No. 8,361,499, which is a continuation of U.S. patent application Ser. No. 12/914,054, filed on Oct. 28, 2010, now U.S. Pat. No. 8,231,898, which is a divisional of U.S. patent application Ser. No. 12/378,586, filed on Feb. 17, 2009, now U.S. Pat. No. 8,142,811, which is a continuation of U.S. patent application Ser. No. 10/660,349, filed on Sep. 11, 2003, now U.S. Pat. No. 7,514,100, which is a continuation of U.S. patent application Ser. No. 10/016,651, filed Oct. 30, 2001, now U.S. Pat. No. 6,733,783, which claims the benefit of U.S. Provisional Application No. 60/244,424, filed Oct. 30, 2000, all hereby incorporated by reference.

FIELD OF THE INVENTION

The present invention is directed to hydrocodone formulations exhibiting a therapeutic effect for at least about 24 hours or more when administered to a human patient.

BACKGROUND OF THE INVENTION

Once-a-day sustained release opioid formulations are disclosed in U.S. Pat. Nos. 5,478,577; 5,672,360; 5,958,459; 6,103,261; 6,143,332; 5,965,161; 5,958,452 and U.S. Pat. No. 5,968,551. All documents cited herein, including the foregoing, are incorporated by reference in their entireties for all purposes.

OBJECTS AND SUMMARY OF THE INVENTION

It is an object of the present invention to substantially improve the efficiency and quality of pain management in human patients experiencing moderate pain.

It is an object of certain embodiments of the present invention to provide bioavailable hydrocodone formulations suitable for once daily administration which substantially improve the efficiency and quality of pain management.

It is an object of certain embodiments of the present invention to provide bioavailable controlled-release hydrocodone formulations suitable for once daily administration which provide a substantially increased duration of effect as compared to immediate release hydrocodone formulations.

It is an object of certain embodiments of the invention to provide orally administrable controlled release opioid formulations suitable for once-a-day administration which provide an early onset of therapeutic effect and which, after rising to a maximum concentration during the dosage interval, provide a relatively flat serum plasma profile, meaning that the plasma level of the opioid provides a $C_{24}/C_{max}$ ratio of about 0.55 to about 1.0, and which provides effective pain relief to the patient.

The above objects and others are attained by virtue of the present invention, which in certain embodiments, provides a solid oral controlled-release dosage form comprising an analgesically effective amount of hydrocodone or a pharmaceutically acceptable salt thereof and a sufficient amount of a controlled release material to render the dosage form suitable for once-a-day administration, the dosage form after administration to a human patient or a population of patients providing a time to peak plasma concentration of hydrocodone in-vivo preferably from about 4 to about 14 hours ($T_{max}$), and providing a $C_{24}/C_{max}$ ratio of 0.55 to 1.0.

In certain embodiments of the invention, the dosage form provides a time to maximum plasma concentration ($T_{max}$) of hydrocodone in-vivo at about 6 to about 12 hours, at about 8 to about 10 hours, at about 4 to about 10 hours or at about 8 to about 14 hours after administration of the dosage form.

In certain embodiments of the invention, the dosage form provides a $C_{24}/C_{max}$ ratio of 0.55 to 1.0, of 0.55 to about 0.85, of 0.55 to 0.75 or of 0.60 to about 0.70.

In certain preferred embodiments, the controlled release dosage form provides an in-vitro release when measured by the USP Basket Method at 100 rpm in 700 ml Simulated Gastric Fluid (SGF) at 37° C. for 1 hour and thereafter switching to 900 ml with Phosphate Buffer to a pH of 7.5 at 37° C., of at least 20% by weight hydrocodone or salt thereof released at 4 hrs, from about 20% to about 65% by weight hydrocodone or salt thereof released at 8 hrs, from about 45% to about 85% by weight hydrocodone or salt thereof released at 12 hrs, and at least 80% by weight hydrocodone or salt thereof released at 24 hours. Although the in-vitro release rate may be either pH-independent or pH-dependent as desired, in preferred embodiments of the invention the release of hydrocodone is pH-independent.

In certain preferred embodiments, the controlled release dosage form provides an in-vitro release of the hydrocodone when measured by the USP Basket method at 100 rpm in 700 ml aqueous buffer at a pH of 1.2 at 37° C. of from 10% to about 45% by weight hydrocodone or salt thereof released at 1 hour.

In certain embodiments of the invention, the dosage form provides an in-vitro release rate, of hydrocodone or a pharmaceutically acceptable salt thereof, when measured by the USP Basket Method at 100 rpm in 900 ml aqueous buffer at a pH of between 1.6 and 7.2 at 37° C. of from 0% to about 35% at 1 hour, from about 10% to about 70% at 4 hours, from about 20% to about 75% at 8 hours, from about 30% to about 80% at 12 hours, from about 40% to about 90% at 18 hours, and greater than about 60% at 24 hours; the in-vitro release rate being substantially independent of pH in that a difference, at any given time, between an amount of opioid released at one pH and an amount released at any other pH, when measured in-vitro using the USP Paddle Method of U.S. Pharmacopeia XXII (1990) at 100 rpm in 900 ml aqueous buffer, is no greater than 10%.

In certain preferred embodiments the sustained release oral dosage form of the present invention provides hydrocodone plasma levels which are effective for 24 hourly dosing, characterized by a $W_{50}$ for the hydrocodone of between 4 and 22 hours. In certain embodiments, the $W_{50}$ is at least 4 hours, preferably at least 12 hours, and more preferably at least 18 hours.

In certain embodiments the sustained release oral dosage form of the present invention comprises a matrix which includes a sustained release material and hydrocodone or a pharmaceutically acceptable salt thereof. In certain embodiments, the matrix is compressed into a tablet and may be optionally overcoated with a coating that in addition to the sustained release material of the matrix may control the release of the hydrocodone or pharmaceutically acceptable salt thereof from the formulation, such that blood levels of active ingredient are maintained within the therapeutic range over an extended period of time. In certain alternate embodiments, the matrix is encapsulated.

In certain embodiments, the sustained release oral dosage form of the present invention comprises a plurality of pharmaceutically acceptable sustained release matrices comprising hydrocodone or a pharmaceutically acceptable salt thereof, the dosage form maintaining the blood plasma levels of hydrocodone within the therapeutic range over an extended period of time when administered to patients.

In certain embodiments the sustained release oral dosage form of the present invention is an osmotic dosage form which comprises a single layer or bilayer core comprising hydrocodone or a pharmaceutically acceptable salt thereof; an expandable polymer; a semipermeable membrane surrounding the core; and a passageway disposed in the semipermeable membrane for sustained release of the hydrocodone or pharmaceutically acceptable salt thereof, such that blood levels of active ingredient are maintained within the therapeutic range over an extended period of time when administered to patients.

In certain preferred embodiments of the invention, there is provided a once-a-day oral controlled release dosage form of hydrocodone which provides a $C_{max}$ of hydrocodone which less than about 60%, less than about 50% or less than about 40% of the $C_{max}$ of an equivalent dose of an immediate release hydrocodone reference formulation (e.g. Lortab®), and which provides effective analgesia during the 24 hour dosage interval.

In certain preferred embodiments of the invention, there is provided a once-a-day oral controlled release hydrocodone dosage form which provides a rate of absorption during the time period from $T_{max}$ to about 24 hours after oral administration of the dosage form which is from about 45% to about 85% of the rate of elimination during the same time period.

In certain preferred embodiments the dosage form of the present invention provides a therapeutic effect for at least about 24 hours after administration of the dosage form.

In certain embodiments, any one or all of the above in-vivo parameters are achieved after a first administration of the dosage form to a human patient or a population of human patients.

In certain alternative embodiments, any one or all of the above in-vivo parameters are achieved after steady state administration of the dosage form to a human patient or a population of human patients.

"Hydrocodone" is defined for purposes of the invention as including hydrocodone free base, as well as pharmaceutically acceptable salts and complexes of hydrocodone.

The term "USP Paddle or Basket Method" is the Paddle and Basket Method described, e.g., in U.S. Pharmacopoeia XXII (1990), herein incorporated by reference.

The term "pH-dependent" for purposes of the present invention is defined as having characteristics (e.g., dissolution) which vary according to environmental pH.

The term "pH-independent" for purposes of the present invention is defined as having characteristics (e.g., dissolution) which are substantially unaffected by pH.

The term "bioavailability" is defined for purposes of the present invention as the extent to which the drug (e.g., hydrocodone) is absorbed from the unit dosage forms.

The term "controlled-release" is defined for purposes of the present invention as the release of the drug (e.g., hydrocodone) at such a rate that blood (e.g., plasma) concentrations are maintained within the therapeutic range but below toxic concentrations over a period of time of about 12 hours or longer.

The term "$C_{max}$" denotes the maximum plasma concentration obtained during the dosing interval.

The term "$C_{24}$" as it is used herein is the plasma concentration of the drug at 24 hours after administration.

The term "$T_{max}$" denotes the time to maximum plasma concentration (Cmax).

The term "$W_{50}$" for purposes of the present invention is the duration over which the plasma concentrations are equal to or greater than 50% of the peak concentration.

The term "$C_{24}/C_{max}$ ratio" is defined for purposes of the present invention as the ratio of the plasma concentration of the drug at 24 hours after administration to the highest plasma concentration of the drug attained within the dosing interval.

The term "semipermeable wall" for purposes of the present invention means that the wall is permeable to the passage of an exterior fluid, such as aqueous or biological fluid, in the environment of use, including the gastrointestinal tract, but impermeable to drug.

The term "minimum effective analgesic concentration" or "MEAC" with respect to concentrations of opioids such as hydrocodone is very difficult to quantify. However, there is generally a minimally effective analgesic concentration of plasma hydrocodone below which no analgesia is provided. While there is an indirect relationship between, e.g., plasma hydrocodone levels and analgesia, higher and prolonged plasma levels are generally associated with superior pain relief. There is a lag time or hysteresis, between the time of peak plasma hydrocodone—levels and the time of peak drug effects. This holds true for the treatment of pain with opioid analgesics in general.

For purposes of the invention, unless further specified, the term "a patient" means that the discussion (or claim) is directed to the pharmacokinetic parameters of an individual patient or subject.

The term "population of patients" means that the discussion (or claim) is directed to the mean pharmacokinetic parameters of at least two patients or subjects.

The term "immediate release hydrocodone reference formulation" for purposes of the present invention, is an equivalent amount of the hydrocodone portion of Lortab®, commercially available from UCB Pharma, Inc, or a pharmaceutical product that provides an immediate release of hydrocodone or a salt thereof.

For purposes of the invention, the controlled release formulations disclosed herein and the immediate release control formulations are dose proportional. In such formulations, the pharmacokinetic parameters (e.g., AUC and $C_{max}$) increase linearly from one dosage strength to another. Therefore the pharmacokinetic parameters of a particular dose can be inferred from the parameters of a different dose of the same formulation.

The term "first administration" means a single dose of the present invention at the initiation of therapy to an individual patient or a patient population.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

The controlled-release oral solid dosage forms of the present invention may be opioid-sparing. It is possible that the controlled-release oral solid dosage forms of the present invention may be dosed at a substantially lower daily dosage in comparison to conventional immediate-release products, with no difference in analgesic efficacy. At comparable daily dosages, greater efficacy may result with the use of the controlled-release oral solid dosage forms of the present invention in comparison to conventional immediate-release products.

DETAILED DESCRIPTION

The above embodiments of the invention can be provided by modifying a wide variety of controlled release formulations known to those skilled in the art. For example, the materials and methods disclosed in U.S. Pat. Nos. 4,861,598, 4,970,075, 5,958,452, and 5,965,161 can be modified to prepare the present invention. These references are hereby incorporated by reference.

Active Agent

The controlled release oral dosage forms of the present invention preferably include from about 0.5 mg to about 1250 mg hydrocodone or an equivalent amount of a pharmaceutically acceptable salt thereof. More preferably, the dosage form contains from about 5 to about 60 mg (e.g. 30 mg) hydrocodone or salt thereof. Suitable pharmaceutically acceptable salts of hydrocodone include hydrocodone bitartrate, hydrocodone bitartrate hydrate, hydrocodone hydrochloride, hydrocodone p-toluenesulfonate, hydrocodone phosphate, hydrocodone thiosemicarbazone, hydrocodone sulfate, hydrocodone trifluoroacetate, hydrocodone hemipentahydrate, hydrocodone pentafluoropropionate, hydrocodone p-nitrophenylhydrazone, hydrocodone o-methyloxime, hydrocodone semicarbazone, hydrocodone hydrobromide, hydrocodone mucate, hydrocodone oleate, hydrocodone phosphate dibasic, hydrocodone phosphate monobasic, hydrocodone inorganic salt, hydrocodone organic salt, hydrocodone acetate trihydrate, hydrocodone bis(heptafuorobutyrate), hydrocodone bis(methylcarbamate), hydrocodone bis(pentafluoropropionate), hydrocodone bis(pyridine carboxylate), hydrocodone bis(trifluoroacetate), hydrocodone chlorhydrate, and hydrocodone sulfate pentahydrate. Preferably, the hydrocodone is present as the bitartrate salt.

The dosage forms of the present invention may further include one or more additional drugs which may or may not act synergistically with the hydrocodone analgesics of the present invention. Examples of such additional drugs include non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflurisal, flufenisal, piroxicam, sudoxicam or isoxicam, and the like. Such non-steroidal anti-inflammatory agents also include cyclo-oxygenase inhibitors such as celecoxib (SC-58635), DUP-697, flosulide (CGP-28238), meloxicam, 6-methoxy-2 naphthylacetic acid (6-MNA), Vioxx (MK-966), nabumetone (prodrug for 6-MNA), nimesulide, NS-398, SC-5766, SC-58215, and T-614. as amantadine (1-aminoadamantine), and memantine (3,5 dimethylaminoadamantone), their mixtures and pharmaceutically acceptable salts thereof.

Other additional drugs include nontoxic NMDA receptor antagonists such dextrorphan, dextromethorphan, 3-(1-naphthalennyl)-5-(phosphonomethyl)-L-phenylalanine, 3-(1-naphthalenyl)-5-(phosphonomethyl)-DL-phenylalanine, 1-(3,5-dimethylphenyl)naphthalene, and 2-(3,5-dimethylphenyl) naphthalene, 2SR,4RS-4-(((1H-Tetrazol-5-yl)methyl)oxylpiperidine-2-carboxylic acid; 2SR,4RS-4-((((1H-Tetrazol-5-yl)uethyl)oxylmethyl)piperidine-2-carboxylic acid; E and Z 2SR-4-(O-(1H-Tetrazol-5-yl)methyl)ketoximino)piperidine-2-carboxylic acid; 2SR,4RS-4-((1H-Tetrazol-5-yl)thio)piperidine-2-carboxylic acid; 2SR,4RS-4-(1H-Tetrazol-5-yl)thio)piperidine-2-carboxylic acid; 2SR,4RS-4-(5-mere apto-1H-Tetrazol-1-yl)piperidine-2-carboxylic acid; 2SR,4RS-4-(5-mere apto-2H-Tetrazol-2-yl)piperidine-2-carboxylic acid; 2SR,4RS-4-(5-mercapto-1H-Tetrazol-1-yl) piperidine-2-carboxylic acid; 2SR,4RS-4-(5-mercapto-2H-Tetrazol-2-yl) piperidine-2-carboxylic acid; 2SR,4RS-4-(((1H-Tetrazol-5-yl)thio)methyl)piperidine-2-carboxylic acid; 2SR,4RS-4-((5-mercapto-1H-Tetrazol-1-yl)methyl) piperidine-2-carboxylic acid; or 2SR,4RS-4-(5-mercapto-2H-Tetrazol-2-yl)methyl)piperidine-2-carboxylic acid, their mixtures and pharmaceutically acceptable salts thereof.

Other suitable additional drugs which may be included in the dosage forms of the present invention include acetaminophen, aspirin, neuro-active steroids (such as those disclosed in U.S. Ser. No. 09/026,520, filed Feb. 20, 1998, hereby incorporated by reference) and other non-opioid analgesics.

For example, if a second (non-opioid) drug is included in the formulation, such drug may be included in controlled release form or in immediate release form. The additional drug may be incorporated into the controlled release matrix along with the opioid; incorporated into the controlled release coating; incorporated as a separated controlled release layer or immediate release layer; or may be incorporated as a powder, granulation, etc., in a gelatin capsule with the substrates of the present invention.

In certain preferred embodiments of the present invention, an effective amount of hydrocodone in immediate release form is included in the controlled release unit dose hydrocodone formulation to be administered. The immediate release form of the hydrocodone is preferably included in an amount which is effective to shorten the time to $C_{max}$ of the hydrocodone in the blood (e.g., plasma). The immediate release form of the opioid is preferably included in an amount which is effective to shorten the time to maximum concentration of the opioid in the blood (e.g., plasma), such that the $T_{max}$ is shortened to a time of, e.g., from about 4 to about 10 hours, or from about 6 to about 8 hours. In such embodiments, an effective amount of the hydrocodone in immediate release form may be coated onto the substrates of the present invention. For example, where the extended release hydrocodone from the formulation is due to a controlled release coating, the immediate release layer would be overcoated on top of the controlled release coating. On the other hand, the immediate release layer may be coated onto the surface of substrates wherein the hydrocodone is incorporated in a controlled release matrix. Where a plurality of the sustained release substrates comprising an effective unit dose of the hydrocodone (e.g., multiparticulate systems including pellets, spheres, beads and the like) are incorporated into a hard gelatin capsule, the immediate release portion of the opioid dose may be incorporated into the gelatin capsule via inclusion of the sufficient amount of immediate release hydrocodone as a powder or granulate within the capsule. Alternatively, the gelatin capsule itself may be coated with an immediate release layer of the hydrocodone. One skilled in the art would recognize still other alternative manners of incorporating the immediate release hydromorphone portion into the unit dose. Such alternatives are deemed to be encompassed by the appended claims. By including such an effective amount of immediate release hydrocodone in the unit dose, the experience of relatively higher levels of pain in patients may be significantly reduced.

Dosage Forms

The controlled-release dosage form may optionally include a controlled release material which is incorporated into a matrix along with the hydrocodone, or which is applied as a sustained release coating over a substrate comprising the drug (the term "substrate" encompassing beads, pellets, spheroids, tablets, tablet cores, etc). The controlled release material may be hydrophobic or hydrophilic as desired. The oral dosage form according to the invention may be provided as, for example, granules, spheroids, pellets or other multiparticulate formulations. An amount of the multiparticulates which is effective to provide the desired dose of opioid over time may be placed in a capsule or may be incorporated in any other suitable oral solid form, e.g., compressed into a tablet. On the other hand, the oral dosage form according to the present invention may be prepared as a tablet core coated with a controlled-release coating, or as a tablet comprising a matrix of drug and controlled release material, and optionally other pharmaceutically desirable ingredients (e.g., diluents, binders, colorants, lubricants, etc.). The controlled release dosage form of the present invention may also be prepared as a bead formulation or an osmotic dosage formulation.

Controlled Release Matrix Formulations

In certain preferred embodiments of the present invention, the controlled-release formulation is achieved via a matrix (e.g. a matrix tablet) which includes a controlled-release material as set forth below. A dosage form including a controlled-release matrix provides in-vitro dissolution rates of the opioid within the preferred ranges and that releases the opioid in a pH-dependent or pH-independent manner. The materials suitable for inclusion in a controlled-release matrix will depend on the method used to form the matrix. The oral dosage form may contain between 1% and 80% (by weight) of at least one hydrophilic or hydrophobic controlled release material.

A non-limiting list of suitable controlled-release materials which may be included in a controlled-release matrix according to the invention include hydrophilic and/or hydrophobic materials, such as gums, cellulose ethers, acrylic resins, protein derived materials, waxes, shellac, and oils such as hydrogenated castor oil, hydrogenated vegetable oil. However, any pharmaceutically acceptable hydrophobic or hydrophilic controlled-release material which is capable of imparting controlled-release of the opioid may be used in accordance with the present invention. Preferred controlled-release polymers include alkylcelluloses such as ethylcellulose, acrylic and methacrylic acid polymers and copolymers, and cellulose ethers, especially hydroxyalkylcelluloses (e.g., hydroxypropylmethylcellulose) and carboxyalkylcelluloses. Preferred acrylic and methacrylic acid polymers and copolymers include methyl methacrylate, methyl methacrylate copolymers, ethoxyethyl methacrylates, cynaoethyl methacrylate, aminoalkyl methacrylate copolymer, poly(acrylic acid), poly (methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. Certain preferred embodiments utilize mixtures of any of the foregoing controlled-release materials in the matrices of the invention.

The matrix also may include a binder. In such embodiments, the binder preferably contributes to the controlled-release of the hydrocodone from the controlled-release matrix.

Preferred hydrophobic binder materials are water-insoluble with more or less pronounced hydrophilic and/or hydrophobic trends. Preferred hydrophobic binder materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils, natural and synthetic waxes and polyalkylene glycols. Preferably, the hydrophobic binder materials useful in the invention have a melting point from about 30 to about 200° C., preferably from about 45 to about 90° C. When the hydrophobic material is a hydrocarbon, the hydrocarbon preferably has a melting point of between 25° and 90° C. Of the long chain ($C_8$-$C_{50}$) hydrocarbon materials, fatty (aliphatic) alcohols are preferred. The oral dosage form may contain up to 80% (by weight) of at least one digestible, long chain hydrocarbon.

Preferably, the oral dosage form contains up to 80% (by weight) of at least one polyalkylene glycol. The hydrophobic binder material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30 to about 100° C.

In certain preferred embodiments, a combination of two or more hydrophobic binder materials are included in the matrix formulations. If an additional hydrophobic binder material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable controlled-release matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of opioid release required. The aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the aliphatic alcohol. When a polyalkylene glycol is present in the oral dosage form, then the combined weight of the aliphatic alcohol and the polyalkylene glycol preferably constitutes between 20% and 50% (by wt) of the total dosage.

In one preferred embodiment, the ratio of, e.g., the at least one hydroxyalkyl cellulose or acrylic resin to the at least one aliphatic alcohol/polyalkylene glycol determines, to a considerable extent, the release rate of the opioid from the formulation. A ratio of the hydroxyalkyl cellulose to the aliphatic alcohol/polyalkylene glycol of between 1:2 and 1:4 is preferred, with a ratio of between 1:3 and 1:4 being particularly preferred.

The polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled-release matrix comprises an alkylcellulose (especially ethylcellulose), a $C_{12}$ to $C_{36}$ aliphatic alcohol and, optionally, a polyalkylene glycol.

In addition to the above ingredients, a controlled-release matrix may also contain suitable quantities of other materials, e.g., diluents, lubricants, binders, granulating aids, colorants, flavorants and glidants that are conventional in the pharmaceutical art.

In order to facilitate the preparation of a solid, controlled-release oral dosage form according to this invention there is provided, in a further aspect of the present invention, a process for the preparation of a solid, controlled-release oral dosage form according to the present invention comprising incorporating opioids or a salt thereof in a controlled-release matrix. Incorporation in the matrix may be effected, for example, by (a) forming granules comprising at least one hydrophobic and/or hydrophilic material as set forth above (e.g., a water soluble hydroxyalkyl cellulose) together with the hydrocodone;

(b) mixing the at least one hydrophobic and/or hydrophilic material-containing granules with at least one $C_{12}$-$C_{36}$ aliphatic alcohol, and (c) optionally, compressing and shaping the granules.

The granules may be formed by any of the procedures well-known to those skilled in the art of pharmaceutical formulation. For example, in one preferred method, the granules may be formed by wet granulating hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In certain embodiments, the dosage form comprises a plurality of matrices described above.

The matrices of the present invention may also be prepared via a melt pellitization technique. In such circumstance, the opioid in finely divided form is combined with a binder (also in particulate form) and other optional inert ingredients, and thereafter the mixture is pelletized, e.g., by mechanically working the mixture in a high shear mixer to form the pellets (granules, spheres). Thereafter, the pellets (granules, spheres) may be sieved in order to obtain pellets of the requisite size. The binder material is preferably in particulate form and has a melting point above about 40° C. Suitable binder substances include, for example, hydrogenated castor oil, hydrogenated vegetable oil, other hydrogenated fats, fatty alcohols, fatty acid esters, fatty acid glycerides, and the like.

Controlled-release matrices can also be prepared by, e.g., melt-granulation or melt-extrusion techniques. Generally, melt-granulation techniques involve melting a normally solid hydrophobic binder material, e.g. a wax, and incorporating a powdered drug therein. To obtain a controlled release dosage form, it may be necessary to incorporate a hydrophobic controlled release material, e.g. ethylcellulose or a water-insoluble acrylic polymer, into the molten wax hydrophobic binder material. Examples of controlled-release formulations prepared via melt-granulation techniques are found, e.g., in U.S. Pat. No. 4,861,598, assigned to the Assignee of the present invention and hereby incorporated by reference in its entirety.

The hydrophobic binder material may comprise one or more water-insoluble wax-like thermoplastic substances possibly mixed with one or more wax-like thermoplastic substances being less hydrophobic than said one or more water-insoluble wax-like substances. In order to achieve controlled release, the individual wax-like substances in the formulation should be substantially non-degradable and insoluble in gastrointestinal fluids during the initial release phases. Useful water-insoluble wax-like binder substances may be those with a water-solubility that is lower than about 1:5,000 (w/w).

In addition to the above ingredients, a controlled release matrix may also contain suitable quantities of other materials, e.g., diluents, lubricants, binders, granulating aids, colorants, flavorants and glidants that are conventional in the pharmaceutical art in amounts up to about 50% by weight of the particulate if desired. The quantities of these additional materials will be sufficient to provide the desired effect to the desired formulation.

The preparation of a suitable melt-extruded matrix according to the present invention may, for example, include the steps of blending the opioid analgesic, together with a controlled release material and preferably a binder material to obtain a homogeneous mixture. The homogeneous mixture is then heated to a temperature sufficient to at least soften the mixture sufficiently to extrude the same. The resulting homogeneous mixture is then extruded, e.g., using a twin-screw extruder, to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides controlled release of the therapeutically active agent for a time period of from about 8 to at least about 24 hours.

An optional process for preparing the melt extrusioned formulations of the present invention includes directly metering into an extruder a hydrophobic controlled release material, a therapeutically active agent, and an optional binder material; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

Plasticizers, such as those described herein, may be included in melt-extruded matrices. The plasticizer is preferably included as from about 0.1 to about 30% by weight of the matrix. Other pharmaceutical excipients, e.g., talc, mono or poly saccharides, colorants, flavorants, lubricants and the like may be included in the controlled release matrices of the present invention as desired. The amounts included will depend upon the desired characteristic to be achieved.

The diameter of the extruder aperture or exit port can be adjusted to vary the thickness of the extruded strands. Furthermore, the exit part of the extruder need not be round; it can be oblong, rectangular, etc. The exiting strands can be reduced to particles using a hot wire cutter, guillotine, etc.

A melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic controlled release material as described herein. Preferably the melt-extruded multiparticulates will be of a range of from about 0.1 to about 12 mm in length and have a diameter of from about 0.1 to about 5 mm In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared that include an effective amount of melt-extruded multiparticulates within a capsule. For example, a plurality of the melt-extruded multiparticulates may be placed in a gelatin capsule in an amount sufficient to provide an effective controlled release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Arthur Osol, editor), 1553-1593 (1980), incorporated by reference herein.

In yet another preferred embodiment, the extrudate can be shaped into tablets as set forth in U.S. Pat. No. 4,957,681 (Klimesch, et. al.), hereby incorporated by reference.

Optionally, the controlled-release matrix multiparticulate systems or tablets can be coated, or the gelatin capsule can be further coated, with a controlled release coating such as the controlled release coatings described above. Such coatings preferably include a sufficient amount of hydrophobic and/or hydrophilic controlled-release material to obtain a weight gain level from about 2 to about 25 percent, although the overcoat may be greater depending upon, e.g., the physical properties of the particular opioid analgesic used and the desired release rate, among other things.

The dosage forms of the present invention may further include combinations of melt-extruded multiparticulates containing one or more opioid analgesics. Furthermore, the dosage forms can also include an amount of an immediate release therapeutically active agent for prompt therapeutic effect. The immediate release therapeutically active agent may be incorporated, e.g., as separate pellets within a gelatin capsule, or may be coated on the surface of, e.g., melt extruded multiparticulates. The unit dosage forms of the present invention may also contain a combination of, e.g., controlled release beads and matrix multiparticulates to achieve a desired effect.

The controlled-release formulations of the present invention preferably slowly release the therapeutically active agent, e.g., when ingested and exposed to gastric fluids, and then to intestinal fluids. The controlled-release profile of the melt-extruded formulations of the invention can be altered, for example, by varying the amount of controlled-release material, by varying the amount of plasticizer relative to other matrix constituents, hydrophobic material, by the inclusion of additional ingredients or excipients, by altering the method of manufacture, etc.

In other embodiments of the invention, melt-extruded formulations are prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

Typical melt-extrusion production systems suitable for use in accordance with the present invention include a suitable extruder drive motor having variable speed and constant torque control, start-stop controls, and ammeter. In addition, the production system will include a temperature control console which includes temperature sensors, cooling means and temperature indicators throughout the length of the extruder. In addition, the production system will include an extruder such as twin-screw extruder which consists of two counter-rotating intermeshing screws enclosed within a cylinder or barrel having an aperture or die at the exit thereof. The feed materials enter through a feed hopper and are moved through the barrel by the screws and are forced through the die into strands which are thereafter conveyed such as by a continuous movable belt to allow for cooling and being directed to a pelletizer or other suitable device to render the extruded ropes into the multiparticulate system. The pelletizer can consist of rollers, fixed knife, rotating cutter and the like. Suitable instruments and systems are available from distributors such as C.W. Brabender Instruments, Inc. of South Hackensack, N.J. Other suitable apparatus will be apparent to those of ordinary skill in the art.

A further aspect of the invention is related to the preparation of melt-extruded multiparticulates as set forth above in a manner which controls the amount of air included in the extruded product. By controlling the amount of air included in the extrudate, the release rate of the therapeutically active agent from the, e.g., multiparticulate extrudate, can be altered significantly. In certain embodiments, the pH dependency of the extruded product can be altered as well.

Thus, in a further aspect of the invention, the melt-extruded product is prepared in a manner which substantially excludes air during the extrusion phase of the process. This may be accomplished, for example, by using a Leistritz extruder having a vacuum attachment. In certain embodiments the extruded multiparticulates prepared according to the invention using the Leistritz extruder under vacuum provides a melt-extruded product having different physical characteristics. In particular, the extrudate is substantially non-porous when magnified, e.g., using a scanning electron microscope which provides an SEM (scanning electron micrograph). Such substantially non-porous formulations provide a faster release of the therapeutically active agent, relative to the same formulation prepared without vacuum. SEMs of the multiparticulates prepared using an extruder under vacuum appear very smooth, and the multiparticulates tend to be more robust than those multiparticulates prepared without vacuum. In certain formulations, the use of extrusion under vacuum provides an extruded multiparticulate product which is more pH-dependent than its counterpart formulation prepared without vacuum. Alternatively, the melt-extruded product is prepared using a Werner-Pfleiderer twin screw extruder.

In certain embodiments, a spheronising agent is added to a granulate or multiparticulates of the present invention and then spheronized to produce controlled release spheroids. The spheroids are then optionally overcoated with a controlled release coating by methods such as those described herein.

Spheronising agents which may be used to prepare the multiparticulate formulations of the present invention include any art-known spheronising agent. Cellulose derivatives are preferred, and microcrystalline cellulose is especially preferred. A suitable microcrystalline cellulose is, for example, the material sold as Avicel PH 101 (Trade Mark, FMC Corporation). The spheronising agent is preferably included as about 1 to about 99% of the multiparticulate by weight.

In addition to the active ingredient and spheronizing agent, the spheroids may also contain a binder. Suitable binders, such as low viscosity, water soluble polymers, will be well known to those skilled in the pharmaceutical art. However, water soluble hydroxy lower alkylcellulose, such as hydroxypropylcellulose, are preferred.

In addition to the opioid analgesic and spheronising agent, the multiparticulate formulations of the present invention may include a controlled release material such as those described hereinabove. Preferred controlled-release materials for inclusion in the multiparticulate formulations include acrylic and methacrylic acid polymers or copolymers, and ethylcellulose. When present in the formulation, the controlled-release material will be included in amounts of from about 1 to about 80% of the multiparticulate, by weight. The controlled-release material is preferably included in the multiparticulate formulation in an amount effective to provide controlled release of the opioid analgesic from the multiparticulate.

Pharmaceutical processing aids such as binders, diluents, and the like may be included in the multiparticulate formulations. Amounts of these agents included in the formulations will vary with the desired effect to be exhibited by the formulation.

Specific examples of pharmaceutically acceptable carriers and excipients that may be used to formulate oral dosage forms of the present invention are described in the *Handbook of Pharmaceutical Excipients*, American Pharmaceutical Association (1986), incorporated by reference herein.

The multiparticulates may be overcoated with a controlled-release coating including a controlled-release material such as those described hereinabove. The controlled-release coating is applied to a weight gain of from about 5 to about 30%. The amount of the controlled-release coating to be applied will vary according to a variety of factors, e.g., the composition of the multiparticulate and the chemical and/or physical properties of the opioid analgesic (i.e., hydrocodone).

Matrix multiparticulates may also be prepared by granulating the spheronising agent together with the opioid analgesic, e.g. by wet granulation. The granulate is then spheronized to produce the matrix multiparticulates. The matrix multiparticulates are then optionally overcoated with the controlled release coating by methods such as those described hereinabove.

Another method for preparing matrix multiparticulates, for example, by (a) forming granules comprising at least one water soluble hydroxyalkyl cellulose and opioid or an opioid salt; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained-release coating will generally include a water insoluble material such as (a) a wax, either alone or in admixture with a fatty alcohol; or (b) shellac or zein.

Spheroids of the present invention comprise a matrix formulation as described above or bead formulation as described hereinafter having a diameter of between 0.1 mm and 2.5 mm, especially between 0.5 mm and 2 mm.

The spheroids are preferably film coated with a controlled release material that permits release of the opioid (or salt) at a controlled rate in an aqueous medium. The film coat is chosen so as to achieve, in combination with the other stated properties, the in-vitro release rate outlined above (e.g., at least about 12.5% released after 1 hour). The controlled-release coating formulations of the present invention preferably produce a strong, continuous film that is smooth and elegant, capable of supporting pigments and other coating additives, non-toxic, inert, and tack-free.

Preparation of Coated Bead Formulations

In certain embodiments of the present invention the oral solid controlled release dosage form of the present invention comprises a plurality of coated substrates, e.g., inert pharmaceutical beads such as nu pariel 18/20 beads. An aqueous dispersion of hydrophobic material is used to coat the beads to provide for the controlled release of the hydrocodone. In certain embodiments a plurality of the resultant stabilized solid controlled-release beads may be placed in a gelatin capsule in an amount sufficient to provide an effective controlled-release dose when ingested and contacted by an environmental fluid, e.g., gastric fluid or dissolution media.

The stabilized controlled-release bead formulations of the present invention slowly release the opioid analgesic, e.g., when ingested and exposed to gastric fluids, and then to intestinal fluids. The controlled-release profile of the formulations of the invention can be altered, for example, by varying the amount of overcoating with the aqueous dispersion of hydrophobic controlled release material, altering the manner in which the plasticizer is added to the aqueous dispersion of hydrophobic controlled release material, by varying the amount of plasticizer relative to hydrophobic controlled release material, by the inclusion of additional ingredients or excipients, by altering the method of manufacture, etc. The dissolution profile of the ultimate product may also be modified, for example, by increasing or decreasing the thickness of the controlled release coating.

Substrates coated with a therapeutically active agent are prepared, e.g. by dissolving the therapeutically active agent in water and then spraying the solution onto a substrate, for example, nu pariel 18/20 beads, using a Wuster insert. Optionally, additional ingredients are also added prior to coating the beads in order to assist the binding of the opioid to the beads, and/or to color the solution, etc. For example, a product which includes hydroxypropyl methylcellulose, etc. with or without colorant (e.g., Opadry®, commercially available from Colorcon, Inc.) may be added to the solution and the solution mixed (e.g., for about 1 hour) prior to application of the same onto the substrate. The resultant coated substrate may then be optionally overcoated with a barrier agent, to separate the therapeutically active agent from the hydrophobic controlled-release coating.

An example of a suitable barrier agent is one which comprises hydroxypropyl methylcellulose. However, any film-former known in the art may be used. It is preferred that the barrier agent does not affect the dissolution rate of the final product.

The substrates may then be overcoated with an aqueous dispersion of the hydrophobic controlled release material as described herein. The aqueous dispersion of hydrophobic controlled release material preferably further includes an effective amount of plasticizer, e.g. tri-ethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color can be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

The plasticized aqueous dispersion of hydrophobic controlled release material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic material to obtain a predetermined controlled-release of said therapeutically active agent when said coated substrate is exposed to aqueous solutions, e.g. gastric fluid, is preferably applied, taking into account the physical characteristics of the therapeutically active agent, the manner of incorporation of the plasticizer, etc. After coating with the hydrophobic controlled release material, a further overcoat of a film-former, such as Opadry®, is optionally applied to the beads. This overcoat is provided, if at all, in order to substantially reduce agglomeration of the beads.

Another method of producing controlled release bead formulations suitable for about 24-hour administration is via powder layering. U.S. Pat. No. 5,411,745, assigned to the Assignee of the present invention and hereby incorporated by reference in its entirety, teaches preparation of 24-hour morphine formulations prepared via powder layering techniques utilizing a processing aid consisting essentially of hydrous lactose impalpable. The powder-layered beads are prepared by spraying an aqueous binder solution onto inert beads to provide a tacky surface, and subsequently spraying a powder that is a homogenous mixture of morphine sulfate and hydrous lactose impalpable onto the tacky beads. The beads are then dried and coated with a hydrophobic material such as those described hereinabove to obtain the desired release of drug when the final formulation is exposed to environmental fluids. An appropriate amount of the controlled release beads are then, e.g. encapsulated to provide a final dosage form which provides effective plasma concentrations of morphine for about 24 hours.

Controlled Release Osmotic Dosage

Controlled release dosage forms according to the present invention may also be prepared as osmotic dosage formulations. The osmotic dosage forms preferably include a bilayer core comprising a drug layer and a delivery or push layer, wherein the bilayer core is surrounded by a semipermeable wall and optionally having at least one passageway disposed therein. In certain embodiments, the bilayer core comprises a drug layer with hydrocodone or a salt thereof and a displacement or push layer. In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n \cdot H_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the hydrocodone or pharmaceutically acceptable salt thereof from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose represented by a member selected from the group consisting of hydroxypropylmethylcellulose, hydroxypropylethylcellulose, hydroxypropylisopropylcellulose, hydroxypropylbutylcellulose, and hydroxypropylpentylcellulose.

The push layer optionally may comprise a nontoxic colorant or dye. Examples of colorants or dyes include but are not limited to Food and Drug Administration Colorant (FD&C), such as FD&C No. 1 blue dye, FD&C No. 4 red dye, red ferric oxide, yellow ferric oxide, titanium dioxide, carbon black, and indigo.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain alternative embodiments, the dosage form comprises an homogenous core comprising hydrocodone or a pharmaceutically acceptable salt thereof, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The homogenous core is surrounded by a semipermeable wall having a passageway (as defined above) for the release of the hydrocodone or pharmaceutically acceptable salt thereof.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Souriraj an in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ ($cm^2$/hr·atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder as described above.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

Coatings

The dosage forms of the present invention may optionally be coated with one or more coatings suitable for the regulation of release or for the protection of the formulation. In one embodiment, coatings are provided to permit either pH-dependent or pH-independent release, e.g., when exposed to gastrointestinal fluid. When a pH-independent coating is desired, the coating is designed to achieve optimal release regardless of pH-changes in the environmental fluid, e.g., the GI tract. Other preferred embodiments include a pH-dependent coating that releases the opioid in desired areas of the gastro-intestinal (GI) tract, e.g., the stomach or small intestine, such that an absorption profile is provided which is capable of providing at least about twelve hour and preferably up to twenty-four hour analgesia to a patient. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings may also impart a repeat-action effect whereby unprotected drug is coated over an enteric coat and is released in the stomach, while the remainder, being protected by the enteric coating, is released further down the gastrointestinal tract. Coatings which are pH-dependent may be used in accordance with the present invention include a controlled release material such as, e.g., shellac, cellulose acetate phthalate (CAP), polyvinyl acetate phthalate (PVAP), hydroxypropyl methylcellulose phthalate, and methacrylic acid ester copolymers, zein, and the like.

In another preferred embodiment, the present invention is related to a stabilized solid controlled dosage form comprising an opioid coated with a hydrophobic controlled release material selected from (i) an alkylcellulose; (ii) an acrylic polymer; or (iii) mixtures thereof. The coating may be applied in the form of an organic or aqueous solution or dispersion.

In certain preferred embodiments, the controlled release coating is derived from an aqueous dispersion of the hydrophobic controlled release material. The coated substrate containing the opioid(s) (e.g., a tablet core or inert pharmaceutical beads or spheroids) is then cured until an endpoint is reached at which the substrate provides a stable dissolution. The curing endpoint may be determined by comparing the dissolution profile (curve) of the dosage form immediately after curing to the dissolution profile (curve) of the dosage form after exposure to accelerated storage conditions of, e.g., at least one month at a temperature of 40° C. and a relative humidity of 75%. These formulations are described in detail in U.S. Pat. Nos. 5,273,760 and 5,286,493, assigned to the Assignee of the present invention and hereby incorporated by reference. Other examples of controlled-release formulations and coatings which may be used in accordance with the present invention include Assignee's U.S. Pat. Nos. 5,324,351; 5,356,467, and 5,472,712, hereby incorporated by reference in their entirety.

In preferred embodiments, the controlled release coatings include a plasticizer such as those described herein.

In certain embodiments, it is necessary to overcoat the substrate comprising the opioid analgesic with a sufficient amount of the aqueous dispersion of e.g., alkylcellulose or acrylic polymer, to obtain a weight gain level from about 2 to about 50%, e.g., about 2 to about 25% in order to obtain a controlled-release formulation. The overcoat may be lesser or greater depending upon the physical properties of the therapeutically active agent and the desired release rate, the inclusion of plasticizer in the aqueous dispersion and the manner of incorporation of the same, for example.

Alkylcellulose Polymers

Cellulosic materials and polymers, including alkylcelluloses are controlled release materials well suited for coating the substrates, e.g., beads, tablets, etc. according to the invention. Simply by way of example, one preferred alkylcellulosic polymer is ethylcellulose, although the artisan will appreciate that other cellulose and/or alkylcellulose polymers may be readily employed, singly or on any combination, as all or part of a hydrophobic coatings according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the controlled release material comprising the controlled-release coating is a pharmaceutically acceptable acrylic polymer, including but not limited to acrylic acid and methacrylic acid copolymers, methyl methacrylate copolymers, ethoxyethyl methacrylates, cynaoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Röhm Tech, Inc. There are several different types of Eudragit®. For example, Eudragit E is an example of a methacrylic acid copolymer which swells and dissolves in acidic media. Eudragit L is a methacrylic acid copolymer which does not swell at about pH<5.7 and is soluble at about pH>6. Eudragit S does not swell at about pH<6.5 and is soluble at about pH>7. Eudragit RL and Eudragit RS are water swellable, and the amount of water absorbed by these polymers is pH-dependent, however, dosage forms coated with Eudragit RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a controlled-release formulation having a desirable dissolution profile. Desirable controlled-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic controlled release material, the inclusion of an effective amount of a plasticizer in the aqueous dispersion of hydrophobic material will further improve the physical properties of the controlled-release coating. For example, because ethylcellulose has a relatively high glass transition temperature and does not form flexible films under normal coating conditions, it is preferable to incorporate a plasticizer into an ethylcellulose coating containing controlled-release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tibutyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

In certain embodiments, the addition of a small amount of talc to the controlled release coating reduces the tendency of the aqueous dispersion to stick during processing, and acts as a polishing agent.

The release of the therapeutically active agent from the controlled-release formulation of the present invention can be further influenced, i.e., adjusted to a desired rate, by the addition of one or more release-modifying agents, or by providing one or more passageways through the coating. The ratio of hydrophobic controlled release material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The controlled-release coatings of the present invention can also include erosion-promoting agents such as starch and gums.

The controlled-release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer. In certain preferred embodiments, the release-modifying agent is selected from hydroxypropylmethylcellulose, lactose, metal stearates, and mixtures of any of the foregoing.

The controlled-release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864, all of which are hereby incorporated by reference. The passageway can have any shape such as round, triangular, square, elliptical, irregular, etc.

DETAILED DESCRIPTION OF THE PREFERRED EMBODIMENTS

The following examples illustrate various aspects of the present invention. They are not meant to be construed to limit the claims in any manner whatsoever.

Example 1

Hydrocodone sustained release tablets were produced with the formula set forth in Table 1A below:

TABLE 1A

| Ingredient | Amt/unit (mg) | Amt/batch (gram) |
|---|---|---|
| Hydrocodone Bitartrate | 30.0 | 150.0 |
| Spray Dried Lactose | 90.0 | 450.0 |
| Povidone | 8.0 | 40.0 |
| Eudragit RS30D (Solids) | 30.0 | 150.0 |
| Triacetin | 6.0 | 30.0 |
| Stearyl Alcohol | 50.0 | 250.0 |
| Talc | 4.0 | 20.0 |
| Magnesium Stearate | 2.0 | 10.0 |
| Opadry Red YS1-15597-A | 10.0 | 50.0 |
| Purified Water | * | * |
| Total | 230.0 | 1150.0 |

* Used for processing and remains in product as residual moisture only.

According to the following procedure:
1. Granulation: Spray the Eudragit/Triacetin dispersion onto the Hydrocodone Bitartrate, Spray Dried Lactose and Povidone using a fluid bed granulator.
2. Milling: Discharge the granulation and pass through a mill
3. Waxing: Melt the stearyl alcohol and add to the milled granulation using a mixer. Allow to cool.
4. Milling: Pass the cooled granulation through a mill
5. Lubrication: Lubricate the granulation with talc and magnesium stearate using a mixer.
6. Compression: Compress the granulation into tablets using a tablet press
7. Film Coating: Apply an aqueous film coat to the tablets The tablets were then tested for dissolution using the following procedure:
1. Apparatus USP Type I (Basket), 100 rpm.
2. Medium 700 ml SGF for first 55 minutes, thereafter made 900 ml with Phosphate Buffer to pH 7.5.
3. Sampling time 1, 2, 4, 8, and 12 hours.
4. Analytical High Performance Liquid Chromatography.

The dissolution parameters are set forth in Table 1B below:

TABLE 1B

| Time (hour) | % Dissolved |
|---|---|
| 1 | 25.5 |
| 2 | 31.7 |
| 4 | 41.5 |
| 8 | 54.7 |
| 12 | 65.0 |

Example 2

Hydrocodone sustained release tablets were produced with the formula set forth in Table 2A below:

TABLE 2A

| Ingredient | Amt/unit (mg) | Amt/batch (gram) |
|---|---|---|
| Hydrocodone Bitartrate | 15.0 | 187.5 |
| Eudragit RSPO | 78.0 | 975.0 |
| Stearyl Alcohol | 27.0 | 337.5 |
| Total | 120.0 | 1500.0 |

According to the following procedure:
1. Milling: Pass stearyl alcohol flakes through a ill.
2. Blending: Mix Hydrocodone Bitartrate, Eudragit, and milled Stearyl Alcohol.

3. Extrusion: Continuously feed the blended material into a twin screw extruder and collect the resultant strands on a conveyor.
4. Cooling: Allow the strands to cool a Conveyor.
5. Pelletizing: Cut the cooled strands into pellets using a Pelletizer.
6. Screening: Screen the pellets and collect desired sieve portion.

Dissolution Method:
1. Apparatus USP Type I (Basket), 100 rpm.
2. Medium 700 mL SGF for first hour, thereafter made 900 mL with Phosphate Buffer to pH 7.5.
3. Sampling time 1, 2, 4, 8, and 12 hours.
4. Analytical High Performance Liquid Chromatography.

The dissolution parameters are set forth in Table 2B below:

TABLE 2B

| Time (hour) | % Dissolved SGF/SIF |
|---|---|
| 1 | 19.5 |
| 2 | 26.3 |
| 4 | 38.2 |
| 8 | 54.0 |
| 12 | 63.8 |

Example 3

Hydrocodone sustained release osmotic tablets are produced with the formula set forth in Table 3A below:

TABLE 3A

| Ingredient | Percentage |
|---|---|
| Drug Layer: | Percentage of Drug Layer |
| Hydrocodone Bitartrate | 25.4 |
| Polyethylene oxide | 70.1 |
| Povidone | 4 |
| Magnesium Stearate | 0.5 |
| Displacement Layer: | Percentage of Displacement Layer |
| Polyethylene oxide | 68.57 |
| Sodium chloride | 26 |
| Hydroxypropylmethylcellulose | 4.5 |
| Ferric Oxide | 0.6 |
| Magnesium Stearate | 0.25 |
| BHT | 0.08 |
| Semipermeable Wall: | Percentage of Semipermeable Wall |
| Cellulose acetate | 95 |
| Polyethylene glycol | 5 |

The dosage form having the above formulation is prepared according to the following procedure:

Requisite amounts of hydrocodone bitartrate, of poly(ethylene oxide) possessing a 200,000 average molecular weight, and poly(vinyl pyrrolidone) are added to a planetary mixing bowl and are mixed. Then, denatured anhydrous ethyl alcohol is slowly added to the blended materials with continuous mixing for 15 minutes to provide for a wet granulation. Next, the freshly prepared wet granulation is passed through a 20 mesh screen, allowed to dry at room temperature, and passed through a 16 mesh screen. Next, the granulation is transferred to a planetary mixer, mixed and lubricated with the requisite amount of magnesium stearate.

A push composition is prepared as follows: first, a binder solution is prepared by dissolving the requisite amount of hydroxypropylmethylcellulose in of water. Next, butylated hydroxytoluene is dissolved in of denatured anhydrous alcohol. The hydroxypropylmethylcellulose/water solution is added to the butylated hydroxytoluene/alcohol solution with continuous mixing. Next, the binder solution preparation is completed by adding the remaining hydroxypropyl-methylcellulose/water solution to the butylated hydroxytoluene/alcohol solution, again with continuous mixing.

Next, a requisite amount of sodium chloride is sized using a Quadro Comil® mill, used to reduce the particle size of the sodium chloride. The materials are sized with a 21 mesh screen. Next, ferric oxide is passed through a 40 mesh screen. Then, all the screened materials, of pharmaceutically acceptable poly(ethylene oxide) comprising a 7,000,000 average molecular weight, and hydroxypropylmethylcellulose is added to a Glatt Fluid Bed Granulator bowl. The bowl is attached to the granulator and the granulation process is initiated for effecting granulation. Then, the binder solution is sprayed onto the powder.

At the end of the solution spraying, the resultant coated granulated particles are subjected to a drying process. The coated granules are sized using a Quadro Comil with an 8 mesh screen. The granulation is mixed and lubricated with a requisite amount of magnesium stearate.

Next, the hydrocodone bitartrate drug composition and the push composition is compressed into bilayer tablets on the Kilian® Tablet Press. First, the hydrocodone bitartrate composition is added to the die cavity and pre-compressed, then, the push composition is added and the layers are pressed to a bilayered arrangement.

The bilayered arrangement is coated with a semi-permeable wall. The wall forming composition comprises 95% cellulose acetate having a 39.8% acetyl content, and 5% polyethylene glycol. The wall-forming composition is dissolved in an acetone:water (95:5 wt:wt) cosolvent to make a 4% solids solution. The wall-forming composition is sprayed onto and around the bilayers in a 24" Vector Hi® Coater.

Next, two 30 mil (0.762 mm) exit passageways are drilled through the semi-permeable wall to connect the drug layer with the exterior of the dosage system. The residual solvent is removed by drying for 48 hours at 50° C. and 50% humidity. Next, the osmotic dosage forms are dried for 4 hours at 50° C. to remove excess moisture.

Many other variations of the present invention will be apparent to those skilled in the art and are meant to be within the scope of the claims appended hereto.

We claim:
1. A once-a-day oral controlled-release dosage form comprising hydrocodone or a pharmaceutically acceptable salt thereof and a controlled release material comprising a hydrophobic and/or hydrophilic material,
   wherein the controlled release material is included in an effective amount such that the dosage form provides a rate of absorption during the time period from $T_{max}$ to about 24 hours after oral administration of the dosage form to an individual patient which is from about 45% to about 85% of the rate of elimination during the same time period, and
   an in-vitro release rate of hydrocodone or a pharmaceutically acceptable salt thereof, when measured by the USP Basket Method at 100 rpm in 900 ml aqueous buffer at a pH of between 1.6 and 7.2 at 37° C., of from 0% to about 35% at 1 hour, from about 10% to about 70% at 4 hours, from about 20% to about 75% at 8 hours, from about

30% to about 80% at 12 hours, from about 40% to about 90% at 18 hours, and greater than about 60% at 24 hours.

2. The dosage form of claim 1, which provides a $W_{50}$ for the hydrocodone of between 4 and 22 hours.

3. The dosage form of claim 2, wherein the $W_{50}$ is at least 4 hours.

4. The dosage form of claim 2, wherein the $W_{50}$ is at least 12 hours.

5. The dosage form of claim 1, wherein the $W_{50}$ is at least 18 hours.

6. The dosage form of claim 1, which provides a time to peak plasma concentration of hydrocodone at about 6 to about 12 hours after said administration.

7. The dosage form of claim 1, which provides a time to peak plasma concentration of hydrocodone at about 8 to about 10 hours after said administration.

8. The dosage form of claim 1, which provides a time to peak plasma concentration of hydrocodone at about 4 to about 10 hours after said administration.

9. The dosage form of claim 1, which provides a time to peak plasma concentration of hydrocodone at about 8 to about 14 hours after said administration.

10. The dosage form of claim 1, wherein the hydrophobic material is selected from the group consisting of gums, cellulose ethers, acrylic resins, waxes, shellac and oils.

11. The dosage form of claim 1, wherein the controlled release material is incorporated into a matrix along with the hydrocodone.

12. The dosage form of claim 1, wherein the controlled release material is applied as a sustained release coating over a substrate comprising the hydrocodone, and the substrate is selected from the group consisting of beads, pellets, spheroids, tablets and tablet cores.

13. The dosage form of claim 1, wherein said administration is first administration.

14. The dosage form of claim 1, which comprises a core and a coating.

15. The dosage form of claim 14, which is a compressed tablet.

16. A once-a-day oral controlled-release dosage form comprising hydrocodone or a pharmaceutically acceptable salt thereof and a controlled release material comprising a hydrophobic and/or hydrophilic material, wherein the controlled release material is included in an effective amount such that the dosage form provides a mean rate of absorption during the time period from $T_{max}$ to about 24 hours after oral administration of the dosage form to a group of patients which is from about 45% to about 85% of the mean rate of elimination during the same time period, and an in-vitro release rate of hydrocodone or a pharmaceutically acceptable salt thereof, when measured by the USP Basket Method at 100 rpm in 900 ml aqueous buffer at a pH of between 1.6 and 7.2 at 37° C., of from 0% to about 35% at 1 hour, from about 10% to about 70% at 4 hours, from about 20% to about 75% at 8 hours, from about 30% to about 80% at 12 hours, from about 40% to about 90% at 18 hours, and greater than about 60% at 24 hours.

17. The dosage form of claim 16, which provides a mean $W_{50}$ for the hydrocodone of between 4 and 22 hours.

18. The dosage form of claim 17, wherein the mean $W_{50}$ is at least 4 hours.

19. The dosage form of claim 17, wherein the mean $W_{50}$ is at least 12 hours.

20. The dosage form of claim 17, wherein the mean $W_{50}$ is at least 18 hours.

21. The dosage form of claim 17, which provides a mean time to peak plasma concentration of hydrocodone at about 6 to about 12 hours after said administration.

22. The dosage form of claim 16, which provides a mean time to peak plasma concentration of hydrocodone at about 8 to about 10 hours after said administration.

23. The dosage form of claim 16, which provides a mean time to peak plasma concentration of hydrocodone at about 4 to about 10 hours after said administration.

24. The dosage form of claim 16, which provides a mean time to peak plasma concentration of hydrocodone at about 8 to about 14 hours after said administration.

25. The dosage form of claim 16, wherein the hydrophobic material is selected from the group consisting of gums, cellulose ethers, acrylic resins, waxes, shellac and oils.

26. The dosage form of claim 16, wherein the controlled release material is incorporated into a matrix along with the hydrocodone.

27. The dosage form of claim 16, wherein the controlled release material is applied as a sustained release coating over a substrate comprising the hydrocodone, and the substrate is selected from the group consisting of beads, pellets, spheroids, tablets and tablet cores.

28. The dosage form of claim 16, wherein said administration is first administration.

29. The dosage form of claim 16, which comprises a core and a coating.

30. The dosage form of claim 29, which is a compressed tablet.

31. The dosage form of claim 1, wherein said hydrocodone or pharmaceutically acceptable salt thereof is the only active agent in the dosage form.

32. The dosage form of claim 31, wherein the dosage form comprises said pharmaceutically acceptable salt of hydrocodone, and said pharmaceutically acceptable salt of hydrocodone is a bitartrate salt of hydrocodone.

33. The dosage form of claim 16, wherein said hydrocodone or pharmaceutically acceptable salt thereof is the only active agent in the dosage form.

34. The dosage form of claim 33, wherein the dosage form comprises said pharmaceutically acceptable salt of hydrocodone, and said pharmaceutically acceptable salt of hydrocodone is a bitartrate salt of hydrocodone.

* * * * *